United States Patent
Kudschus et al.

Patent Number: 5,914,426
Date of Patent: Jun. 22, 1999

[54] PROCESS FOR THE PREPARATION OF DI-TERT-BUTYL SUCCINATE

[75] Inventors: Martin Kudschus, Givisiez; Olof Wallquist, Marly, both of Switzerland

[73] Assignee: Ciba Specialty Chemicals Corporation, Tarrytown, N.Y.

[21] Appl. No.: 09/060,789

[22] Filed: Apr. 15, 1998

[30] Foreign Application Priority Data

Apr. 15, 1997 [CH] Switzerland ............... 873/97

[51] Int. Cl.$^6$ .................................. C07C 69/34
[52] U.S. Cl. ........................... 560/204; 560/190
[58] Field of Search .............. 44/389; 560/204, 560/190

[56] References Cited

U.S. PATENT DOCUMENTS

| | | | |
|---|---|---|---|
| 3,117,137 | 1/1964 | Maldé et al. | 260/347.5 |
| 4,138,580 | 2/1979 | Umemura et al. | |
| 4,260,810 | 4/1981 | Umemura et al. | |
| 4,730,080 | 3/1988 | Drent. | |
| 5,606,099 | 2/1997 | Darsow. | |

OTHER PUBLICATIONS

A.L. McCloskey and G.S. Fonken, Org. Synth. Coll. vol. 4, 261, (1963).

H. Pielartzik, B. Irmisch–Pielartzik, T. Eicher in Houben–Weyl, vol. E May 1, p. 662 et. seq. (1985).

Hackh's Chemical Dictionary, 4th Ed., Grant et al, Mc–Graw–Hill Book Company, 1969, p. 648.

Slavka Pavlov et al, Bulletin de la Societe Chimique de France, No. 12, Dec. 1974, pp. 2985–2986.

*Primary Examiner*—Margaret Medley
*Attorney, Agent, or Firm*—Kevin T. Mansfield; David R. Crichton

[57] ABSTRACT

A process for the preparation of di-tert-butyl succinate of formula

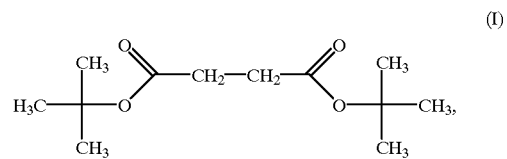

(I)

by proton-catalysed esterification of succinic acid with isobutene, which comprises reacting succinic acid or succinic acid anhydride, or mixtures thereof, with isobutene in the presence of a water-containing acid esterification catalyst, with the proviso that sulfuric acid is used in a concentration of not more than 95% by weight.

By this process it is possible to prepare di-tert-butyl succinate by reacting succinic acid or succinic acid anhydride, or corresponding mixtures of succinic acid and succinic acid anhydride, with isobutene butene with reduced evolution of heat and at the same time with increased yield and improved purity of the end product.

6 Claims, No Drawings

PROCESS FOR THE PREPARATION OF DI-TERT-BUTYL SUCCINATE

The present invention relates to an improved process for the preparation of di-tert-butyl succinate of formula

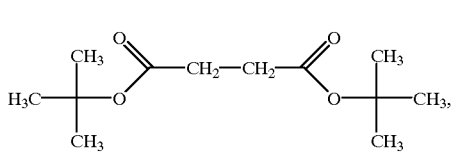

(I)

by proton-catalysed esterification of succinic acid with isobutene.

The preparation of tert-alkylate from carboxylic acids with alkenes in the presence of a concentrated acid, either with or without the addition of aprotic organic cosolvents, such as diethyl ether or dioxane (A. L. McCloskey and G. S. Fonken, Org. Synth. Coll. Vol. 4, 261 (1963), is known.

The esterification of succinic acid with isobutene in the presence of concentrated sulfuric acid and tert-butanol as protic cosolvent is furthermore described by H. Pielartzik, B. Irmisch-Piellartzik, T. Eicher in Houben-Weyl, Vol. E5/1, p. 662 et seq. (1985).

A disadvantage for the technical application of this process is the high evolution of heat during the addition of the concentrated sulfuric acid, which is very difficult to control, especially in large scale production, and which results in safety risks as well as in considerable variations in yield and quality. Polymerisation products of isobutene are formed, for example, the separation of which from the di-tert-butyl succinate is difficult and therefore economically disadvantageous. In addition, the necessary working up is time-, work- and energy-consuming. Preventive measures for controlling the heat which is being released require cooling systems involving complicated apparatus and a correspondingly slow inflow speed of the sulfuric acid. The resultant more costly infrastructure, long reaction time and bad reproducibility of the process are economically disadvantageous.

The object of this invention is therefore to overcome the above shortcomings and to provide a robust and stable process which is economically attractive.

Accordingly, this invention relates to an improved process for the preparation of di-tert-butyl succinate of formula

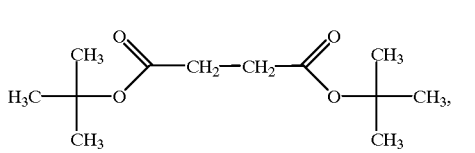

(I)

by proton-catalysed esterification of succinic acid with isobutene, which comprises reacting succinic acid or succinic acid anhydride, or mixtures thereof, with isobutene in the presence of a water-containing acid esterification catalyst, with the proviso that sulfuric acid is used in a concentration of not more than 95% by weight.

The molar ratio of succinic acid or succinic acid anhydride, or of mixtures thereof, to isobutene is usually chosen in the range from 1:2 to 1:50, preferably from 1:6 to 1:13.

The molar ratio of succinic acid to succinic acid anhydride in the mixture is usually chosen in the range from 1:100 to 100:1, preferably from 8:2 to 2:8 and, particularly preferably, from 1:1.

According to this invention, water-containing acid esterification catalysts are used, with the proviso that sulfuric acid is used in a concentration of not more than 95% by weight. Usually, 40 to 90, preferably 40 to 80 and, particularly preferably, 50 to 75% by weight, aqueous mineral acids are used, for example sulfuric acid, phosphoric acid, or organic sulfonic acids, such as methanesulfonic acid.

When using succinic acid, it is preferred to use 65 to 75% by weight aqueous sulfuric acid and, when using succinic acid anhydride, 55 to 65% by weight aqueous sulfuric acid.

0.1 to 1.3 mol of esterification catalyst are usually used per mol of succinic acid or succinic acid anhydride or of a mixture thereof.

It is particularly preferred to use 0.5 to 0.8 mol of sulfuric acid per mol of succinic acid or succinic acid anhydride.

The esterification is normally carried out at a temperature range from 263 to 333 K and at a pressure in the range from $(1\times10^5)$ to $(25\times10^5)$ Pa. The reaction temperature is preferably in the range from 283 to 313 K at $(2\times10^5)$ to $(8\times10^5)$ Pa, very particularly preferably from 293 to 303 K, the reaction mixture in the latter case preferably being kept at a pressure in the range from $(3\times10^5)$ to $(6\times10^5)$ Pa.

The reaction is preferably carried out without organic cosolvents or solvents, but it is also possible to carry out the reaction with them.

The choice and amount of the organic solvents or cosolvents depends on the preferred range and is usually in the range from 0.01 to 50% by weight, preferably in the range from 0.01 to 20% by weight and, particularly preferably, in the range from 0.01 to 10% by weight, based on isobutene.

Organic solvents and cosolvents are, for example, aprotic organic solvents, such as orthodichlorobenzene, or aliphatic hydrocarbons, typically hexane, octane, or ligroine, or ethers, for example dioxane, tetrahydrofuran or diethyl ether, or protic solvents, such as tert-alcohols, preferably tert-butanol or tert-amyl alcohol.

The advantages of the novel processs are that the esterification proceeds with considerably less evolution of heat, a high yield of a markedly less impure crude product being obtained at the same time. This makes the elaborate purification processes unnecessary which are required when using di-tert-butyl succinate as a starting product for the preparation of 1,4-diketopyrrolo-[3,4-c]-pyrrole pigments.

The invention is illustrated by the following Examples:

EXAMPLE 1

(aqueous sulfuric acid/educt: succinic acid):

An autoclave is charged with 212.5 g (1.80 mol) of succinic acid and then 935 g (16.65 mol) of isobutene are forced in at 263 K jacket temperature. After the addition is complete, 146.4 g (1.08 mol) of 72.3% by weight sulfuric acid are pumped in over 45 minutes at a temperature of 268 to 275 K in the vessel. The reaction mixture is then stirred for 30 minutes at a temperature of 275 to 278 K in the vessel and, after increasing the temperature to 293 to 295 K, it is stirred for another 14 hours at that temperature and at a pressure from $(4\times10^5)$ to $(5\times10^5)$ Pa. This reaction mixture is then forced into an agitated mixture consisting of 1000 g of ice and 300 ml (3 mol) of a 30% by weight sodium hydroxide solution and the autoclave is then flushed with 200–300 ml of petroleum ether which is also added to the mixture of ice/sodium hydroxide solution. The mixture is warmed to room temperature and the organic phase is separated. The aqueous phase is extracted 3 times with 100–150 ml of petroleum ether each and the organic phases are then combined. The organic phases are concentrated in a rotary evaporator at a bath temperature of 323 K and ($3\times10^3$) Pa (final value). To purify the crude product, it is distilled overhead, with addition of about 0.5 g of magnesium oxide, via a 30 cm packed column (Raschig rings 5×5 mm) under vacuum. This gives 358.2 g (86.4% of theory) of di-tert-butyl succinate (b.p.: 0.8–0.9 Pa at 321 to 324 K) of 99.0% purity (percent per area), determined by gas chromatography, corresponding to 85.6% of theory à 10%.

Heat evolving during the addition of sulfuric acid: −26 KJ/mol, total reaction heat: −108 KJ/mol of succinic acid.

EXAMPLE 2

(Comparison with the state of the art in H. Pielartzik, B. lrmisch-Piellartzik, T. Eicher in Houben-Weyl, Vol. E5/1, p. 662 et seq. (1985), where concentrated sulfuric acid and tert-butanol are used as cosolvent for the esterification of succinic acid with isobutene):

An autoclave is charged with 212.5 g (1.80 mol) of succinic acid and 166.8 g (2.25 mol) of tert-butanol and then 808 g (14.40 mol) of isobutene are forced in at 263 K jacket temperature. After the addition is complete, 108.1 g (1.08 mol) of 98% sulfuric acid are pumped in over 70 minutes at a temperature of 268 to 275 K in the vessel. The reaction mixture is then stirred for 30 minutes at a temperature of 275 to 278 K in the vessel and, after increasing the temperature to 293 to 295 K, it is stirred for another 14 hours at that temperature and at a pressure from ($4\times10^5$) to ($5\times10^5$) Pa. The reaction mixture is then forced into an agitated mixture consisting of 1000 g of ice and 300 ml (3 mol) of 30% sodium hydroxide solution and the autoclave is then flushed with 200–300 ml of petroleum ether which is also added to the mixture of ice/sodium hydroxide solution. The mixture is warmed to room temperature and the organic phase is separated. The aqueous phase is extracted 3 times with 100–150 ml of petroleum ether each and the organic phases are then combined. The organic phases are concentrated in a rotary evaporator at a bath temperature of 323 K and ($3\times10^3$) Pa (final value). To purify the crude product it is fractionally distilled, with addition of about 0.5 g of magnesium oxide, via a 30 cm packed column (Raschig rings 5×5 mm) under vacuum. The ester content of the individual fractions is determined by gas chromatography. Fractions having ester contents of <97% by weight are distilled again. After a total of 3 distillations, 329.3 g (79.4% of theory) of di-tert-butyl succinate are obtained having a 97.2% purity (percent per area), determined by gas chromatography, corresponding to 7.2% of theory à 100%.

Heat evolving during the addition of sulfuric acid: −77 KJ/mol, total reaction heat: −120 KJ/mol of succinic acid.

EXAMPLE 3

(Educt: succinic acid anhydride):

An autoclave is charged with 190.2 g (1.90 mol) of succinic acid anhydride and then 986 g (17.58 mol) of isobutene are forced in at 263 K jacket temperature. After the addition is complete, 186.4 g (1.14 mol) of 60.0% by weight sulfuric acid are pumped in over 45 minutes at a temperature of 266 to 273 K in the vessel. The reaction mixture is then stirred for 30 minutes at a temperature of 273 to 278 K in the vessel and, after increasing the temperature to 293 to 295 K, it is stirred for another 14 hours at that temperature and at a pressure from ($4\times10^5$) to ($5\times10^5$) Pa. The reaction mixture is then forced into an agitated mixture consisting of 1000 g of ice and 315 ml (3.15 mol) of a 30% by weight sodium hydroxide solution and the autoclave is then flushed with 200–300 ml of petroleum ether which is also added to the mixture of ice/sodium hydroxide solution. The mixture is warmed to room temperature and the organic phase is separated. The aqueous phase is extracted 3 times with 100–150 ml of petroleum ether each and the organic phases are then combined. The organic phases are concentrated in a rotary evaporator at a bath temperature of 323 K and ($3\times10^3$) Pa (final value). To purify the crude product, it is distilled overhead, with addition of about 0.5 g of magnesium oxide, via a 30 cm packed column (Raschig rings 5×5 mm) under vacuum. This gives 385.0 g (88.0% of theory) of di-tert-butyl succinate (b.p: 0.4–0.6 Pa at 320 to 323 K) of 99.6% purity (percent per area), determined by gas chromatography, corresponding to 87.6% of theory à 100%.

Heat evolving during the addition of sulfuric acid: −23 KJ/mol, total reaction heat: −145 KJ/mol of succinic acid anhydride.

EXAMPLE 4

(Elevated reaction temperature+shorter reaction time):

An autoclave is charged with 212.5 g (1.80 mol) of succinic acid and then 943 g (16.81 mol) of isobutene are forced in at 273 K jacket temperature. After the addition is complete, 149.2 g (1.08 mol) of 71.0% by weight of sulfuric acid are pumped in over 45 minutes at a temperature of 275 to 283 K in the vessel. The jacket temperature is then increased to about 298 K and the reaction mixture is stirred for 7 hours at a temperature of 298±0.5 K in the vessel and at a pressure of ($3\times10^5$) to ($5\times10^5$) Pa. This reaction mixture is forced into a stirred mixture consisting of 500 g of ice, 500 g of water and 300 ml (3 mol) of 30% sodium hydroxide solution and the autoclave is then flushed with 200–300 ml of petroleum ether which is also added to the mixture of ice/water/sodium hydroxide solution. The mixture is warmed to room temperature and the organic phase is separated. The aqueous phase is extracted 3 times with 100–150 ml of petroleum ether each and the organic phases are then combined. The organic phases are concentrated in a rotary evaporator at a bath temperature of 323 K and ($3\times10^3$) Pa (final value). To purify the crude product, it is distilled overhead, with addition of about 0.5 g of magnesium oxide, via a 30 cm packed column (Raschig rings 5×5 mm) under vacuum. This gives 360.7 g (87.0% of theory) of di-tert-butyl succinate (b.p: 0.8–0.9 Pa at 321 to 324 K) of 99.4% purity (percent per area), determined by gas chromatography, corresponding to 86.5% of theory à 100%.

What is claimed is:

1. A process for the preparation of di-tert-butyl succinate of formula

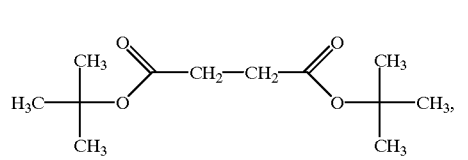

by proton-catalysed esterification of succinic acid or succinic acid anhydride, or mixtures thereof, with isobutene, which comprises contacting succinic acid or succinic acid anhydride, or mixtures thereof, with isobutene in the molar ratio of succinic acid or succinic acid anhydride, or of mixtures thereof, to isobutene of from 1:2 to 1:50, in the presence of 0.1 to 1.3 mole of esterification catalyst per mol of succinic acid or succinic acid anhydride or of a mixture thereof, wherein said catalyst comprises 40 to 80% by weight aqueous sulfuric acid, at a temperature of from 263 to 333 K and at a pressure of $(1\times10^5)$ to $(25\times10^5)$ Pa.

2. A process according to claim 1, wherein the molar ratio of succinic acid or succinic acid anhydride, or of mixtures thereof, to isobutene is from 1:6 to 1:13.

3. A process according to claim 1, wherein the molar ratio of succinic acid to succinic acid anhydride in the mixture is in the range from 8:2 to 2:8.

4. A process according to claim 1, which comprises carrying out the esterification in the temperature range of from 283 to 313 K and at a pressure of $(2\times10^5)$ to $(8\times10^5)$ Pa.

5. A process according to claim 1, which comprises either reacting succinic acid in the presence of 65 to 75% by weight aqueous sulfuric acid, or reacting succinic acid anhydride in the presence of 55 to 65% by weight aqueous sulfuric acid.

6. A process according to claim 1, which comprises using 0.5 to 0.8 mol of esterification catalyst per mol of succinic acid or succinic acid anhydride or of a mixture thereof.

* * * * *